United States Patent [19]

Baehr et al.

[11] 4,061,146
[45] Dec. 6, 1977

[54] TISSUE MACERATING INSTRUMENT

[75] Inventors: Edward F. Baehr, Berea; James E. Burnett, Cleveland, both of Ohio

[73] Assignee: The United States of America as represented by the Administrator of the National Aeronautics and Space Administration, Washington, D.C.

[21] Appl. No.: 677,353

[22] Filed: Apr. 15, 1976

[51] Int. Cl.² ............................................ A61B 17/32
[52] U.S. Cl. .................................................. 128/305
[58] Field of Search ........................................ 128/305

[56] References Cited

U.S. PATENT DOCUMENTS

| | | | |
|---|---|---|---|
| 3,736,938 | 6/1973 | Evvard et al. | 128/305 |
| 3,844,272 | 10/1974 | Banko | 128/305 X |
| 3,906,954 | 9/1975 | Baehr et al. | 128/305 |
| 3,930,505 | 1/1976 | Wallach | 128/305 |
| 3,945,375 | 3/1976 | Banko | 128/305 |
| 3,976,077 | 8/1976 | Kerfoot, Jr. | 128/305 |

*Primary Examiner*—Channing L. Pace
*Attorney, Agent, or Firm*—N. T. Musial; J. A. Mackin; John R. Manning

[57] ABSTRACT

There is disclosed a surgical tissue macerating and removal tool having a rotating rod with a cutting member at one end and disposed in a tube which itself is disposed coaxially in an extension of the tool handle. A frusto-conical member extends into the extension at the cutter member end of the rotating rod with its small end engaging the tube. The portion of the frusto-conical member outside of the extension forms a tissue engaging member and may be cut-off at an angle to the axis of the rod to form a tissue engaging edge. Apertures are provided in the extension adjacent the frusto-conical member so that treatment fluid supplied in the annular space between the tube and the extension may flow to the operative site. An aperture is provided in the frusto-conical member between the extension and the tube so that fluid may also flow into the tube where it mixes with macerated tissue being directed through an aperture in the tube to a passageway which may have suction applied thereto to help remove macerated material. Radially-inwardly extending fins may be provided on the interior surface of the frusto-conical member to inhibit or prevent rotation of the tissue being macerated as, for example, the lens of an eye.

13 Claims, 2 Drawing Figures

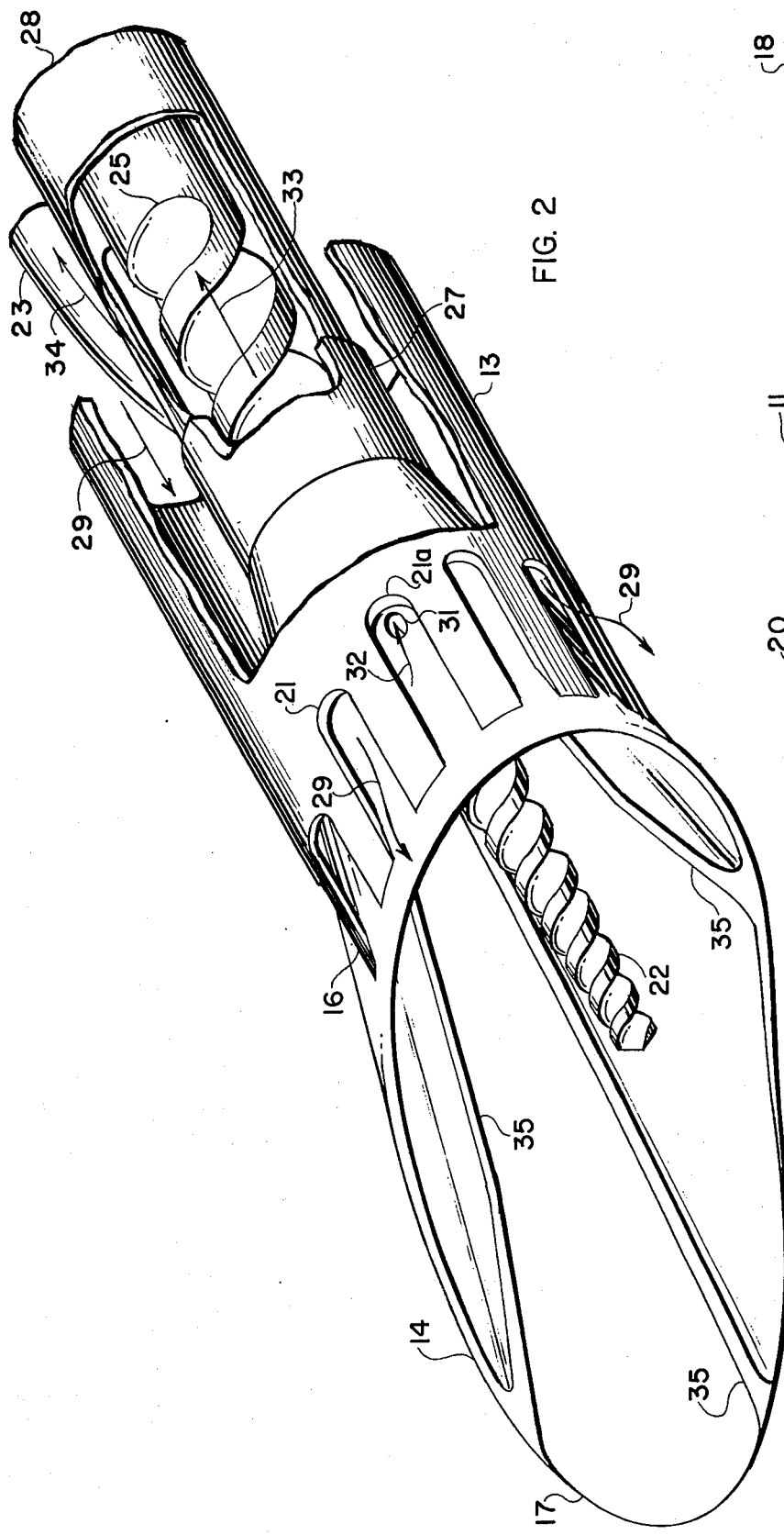
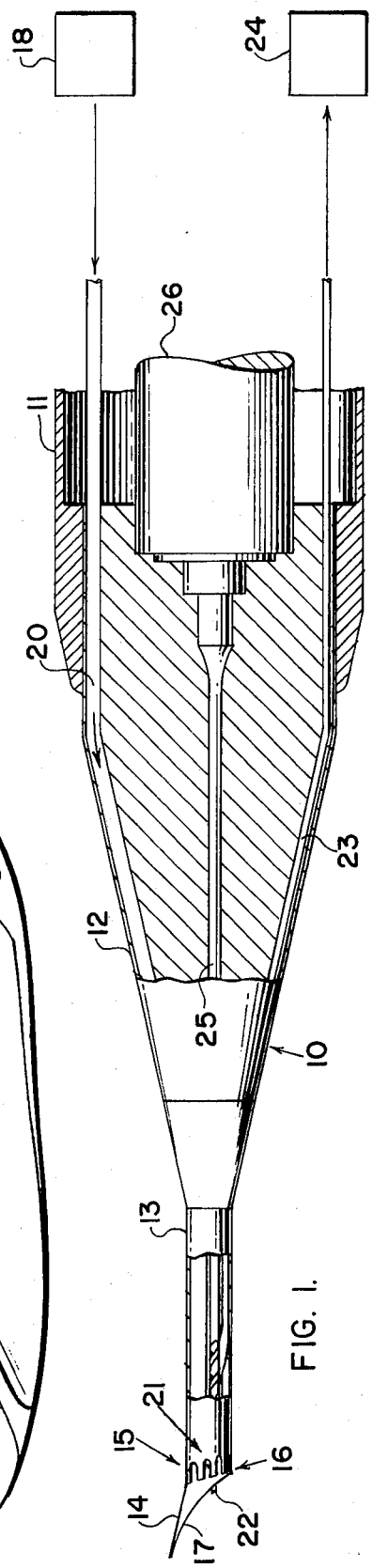
FIG. 2
FIG. 1.

TISSUE MACERATING INSTRUMENT

ORIGIN OF THE INVENTION

This invention was made by employees of the United States Government and may be made or used by the Government of the United States without a payment of any royalties thereon or therfore.

BACKGROUND OF THE INVENTION

The formation of a cataract in a human eye not only causes gradual loss of vision and eventual total blindness but, if allowed to progress to hypermaturity, may cause total degeneration of the eye. Restoring vision to an eye in which a cataract has formed involves completely removing the lens. This is an exceedingly delicate operation and requires a subsequent substantial immobility of the patient for approximately 3 weeks. Because of the relatively large incision made in the eye and the sutures required, any sudden or erratic movement within weeks after the operation may cause the eye to be irreparably damaged.

Accordingly, numerous instruments have been designed to be inserted into the eye through a small puncture to remove lens material or other materials such as blood clot, vitreous opacities, adhesions, and the like. A small puncture requires only one or two sutures, thereby requiring less immobilization time on the part of the patient.

Some instruments utilize vibrating chisel-shaped or pointed members. Some others provide treatment fluid under controlled pressure to the operative site and also provide suction to remove macerated material from the site. Complicated controls such as computers are required when suction is applied to the eye to prevent sudden increases in the suction as, for example, when macerated material blocking the suction passage suddenly breaks loose.

An instrument such as that shown in U.S. Pat. No. 3,736,938 utilizes a combination of an ultrasonically vibrating tube with a rotating cutter bit which has spiral grooves to evacuate macerated material along with used treatment fluid. Many opthamologists, however, are concerned that using ultrasonic energy in the eye may cause damage as yet unknown.

A number of problems occur with regard to rotating a cutting member at high speed where the necessary removal of macerated material is to be accomplished without applying suction to the eye. Some of these problems include heating, loose tolerances required to reduce heating and its effects, and binding of the rotating cutter because of thickening and hardening of the macerated material as it is pumped out of the eye. Of course, the faster the cutter rotates, the more acute these problems become.

It has been found that some tissue, such as a hard cataract, is very difficult to macerate with a surgical tool of the type using a rotating cutter. This appears to occur because the cataract moves from the force from the cutter which is attempting to cut the hard material.

OBJECTS AND SUMMARY OF THE INVENTION

It is an object of the invention to provide an improved tissue macerating tool of the type having a rotating cutter.

It is another object of the invention to provide a tissue macerating tool of the type having a rotating cutter wherein the tissue is drawn towards the cutter member.

It is another object of the invention to provide a tissue macerating instrument wherein the operative tip is provided with structure which resists rotation of the tissue being macerated.

Still another object of the invention is to provide an improved tissue macerating instrument wherein a portion of a treatment fluid being directed to the operative site is redirected to mix with the macerated material to prevent binding of the rotating cutter.

Still another object of the invention is to provide a tissue macerating tool having a formed tissue engaging edge which aids in increasing the rate of maceration of tissue.

DESCRIPTION OF THE DRAWINGS

FIG. 1 is a partial longitudinal section in a partial cutaway view of a tissue macerating instrument embodying the invention.

FIG. 2 is a partial cutaway oblique view of the operative end of a tissue macerating and removal tool embodying the invention.

DESCRIPTION OF A PREFERRED EMBODIMENT

Referring now to FIG. 1, there is shown a surgical tissue macerating and removal tool 10 comprising a handle portion 11, a component support housing 12, an extension 13, and a tissue engaging tip 14. The tissue engaging tip 14 is the exterior portion of a frusto-conical member having a frusto-conical portion 15 which is enclosed within the extension 13 to the right of annular juncture 16 which is the intersection of the extension 13 with the frusto-conical member.

The portion 15 serves as an annular intemediate wall.

The exterior portion 14 of the frusto-conical member has a tissue engaging edge 17 resulting from forming the large end of the frusto-conical portion at an angle to the longitudinal axis of the extension 13. Whether or not the tissue engaging edge 17 is at an angle, it may be conformed so that it may lie closely on a generally spherical surface such as the lens of an eye.

In order to provide treatment fluid to a site at which tissue is being macerated, a fluid such as buffered saline solution is directed from a treatment fluid source 18 through an inflow passageway 20 and out of aperatures 21. Material macerated by a rotating cutter portion 22, together with treatment fluid, is directed up along the cutter and through an outflow passageway 23 to a collector 24. The cutter portion 22 is at the end of a rod 25 rotated by drive means such as an air turbine 26.

The rod 25 may include an archimedes screw portion at the cutter 22, as shown. This arrangement pumps macerated material and treatment fluid out through passageway 23 to collector 24. However, a suction pump may be included in collector 24 in which case the archimedes screw may be eliminated. If desired, the structure to the right of extension 13, as view in FIG. 1, may be substantially indentical to the surgical tool shown in U.S. Pat. No. 3,906,954 which is incorporated herein by reference.

FIG. 2 is an enlarged, oblique view of the tissue engaging tip 14 and the adjacent portion of extension 13 shown partially cut away. Parts in FIG. 2 which correspond to those in FIG. 1 are identified by like numerals.

As shown in FIG. 2, the portion 15 of the frusto-conical member interior to the extension 13 is provided with an annular socket 27 for receiving a tube 28 disposed within the extension 13. The rod 25 which terminates as a tapered cutter portion 22 rotates within tube 28. As described previously, extension 13 intersects the frusto-conical member at annular juncture 16.

With this arrangement, the treatment fluid from passage 20 flows through the annular space between tube 28 and extension 13 and out through the apertures 21 to the operative site. At least one of the apertures, as 21a, communicates with the interior of tube 28 by means of an aperture 31 in the frusto-conical portion 15. This allows some of the treatment fluid from passageway 20 to flow into the interior of tube 28 as indicated by arrow 32 where it mixed with the mixture of macerated tissue and treatment fluid being pumped along the cutter portion 22. This dilution helps to prevent binding of the rotating rod 25 and cutter 22 in the tube 28. The macerated material and treatment fluid pumped up along the cutter 22 flows, as indicated by arrows 33 and 34, through a passageway 23 as described previously.

To inhibit or prevent rotation of the tissue being macerated, particularly the lens of the eye, radially inwardly extending fins 35 are provided on the interior surface of the tissue engaging portion 14 of the frusto-conical member. These fins may, if desired, taper from a minimum height adjacent the tissue engaging edge 17 to a maximum height for a specific longitudinal increment and then taper to zero height where they intersect the frusto-conical portion 15 at its small end.

The passageway 20 is to such size or may have parallel passageways so that the pressure drop of the total inflow system is very low. The size of passageway 23 is selected to control the maximum outflow velocity to prevent sudden reduction of eye pressure should tip 17 become unblocked when there is a low pressure condition in the discharge passage. Thus, the outflow passageway 23 is much smaller than the inflow passageway 20.

From the foregoing, it will be seen that the invention provides a tissue macerating instrument which is especially useful for tough tissue such as hard cataracts. The instrument provides fluid flow paths which advantageously combine fluid with macerated material. Additionally, structure which inhibits rotation of tissue is included.

It will be understood that changes and modifications may be made to the above-described instrument by those skilled in the art without departing from its spirit and scope as set forth in claims appended hereto.

What is claimed is:

1. (amended) In a tissue macerating instrument of the type having a rotatable rod with a cutter member at one end, said rod being disposed in a tube which itself is disposed in an extension of a handle, the improvement comprising:

a frusto-conical member attached at its small end to said extension, the large end being a tissue engaging edge, at least one aperture in said extension adjacent said frusto-conical member;

an annular intermediate wall extending longitudinally between the small end of said frusto-conical member and one end of said tube, *and having* an inflow *aperture* [passageway] in said *intermediate wall* [extension] in communication with said at least one aperture in said extension, [and]

the interior of said tube being in communication with an outflow passageway.

2. The instrument of claim 1 wherein said annular intermediate wall is an extension of said frusto-conical member into said extension.

3. The instrument of claim 1 wherein radially inwardly extending fins are disposed on the inner surface of said frusto-conical member.

4. The instrument of claim 3 wherein said fins increase in height in a direction away from said tissue engaging edge of said frusto-conical member, and are then of constant height for a substantial longitudinal distance.

5. The instrument of claim 1 wherein said tissue engaging edge of said frusto-conical member lies in a plane which is an angle to the axis of the rotatable rod.

6. The instrument of claim 1 wherein said tissue engaging edge of said frusto-conical member is at an angle to the axis of said rotatable rod and is conformed to lie closely on the surface of a generally spherical shaped object.

7. The instrument of claim 1 wherein an aperture is provided in said intermediate wall to redirect said fluid in the space between said tube and said extension to the interior of said tube to mix with macerated material.

8. The instrument of claim 1 wherein the aperture end of said rod is a tapered archimedes screw.

9. The instrument of claim 1 wherein said at least one aperture in said extension comprises a plurality of longitudinal slots.

10. The instrument of claim 1 wherein said rod is longitudinally adjustable.

11. The instrument of claim 1 wherein a portion of said inflow passageway is formed by said extension, said annular intermediate wall and said tube.

12. The instrument of claim 1 wherein said inflow passageway has a total cross-sectional area such that the total pressure drop of the inflow is low, said outflow passageway being substantially smaller than said inflow passageway to prevent sudden reduction of pressure at the operative site.

13. The instrument of claim 1 wherein said inflow passageway comprises a plurality of parallel passageways.

* * * * *

UNITED STATES PATENT OFFICE
CERTIFICATE OF CORRECTION

PATENT NO. : 4,061,146
DATED : 12-6-77
INVENTOR(S) : E. F. BAEHR et al

It is certified that error appears in the above-identified patent and that said Letters Patent are hereby corrected as shown below:

In column 3, line 53, delete --(amended)--.

Column 4, line 8, "and having" line 9, "aperture" and
   "intermediate" should appear in regular type.
      line 9, delete "/passageway/"
      line 10, delete "/extension/"
      line 11, delete "/and/"

Signed and Sealed this

Eleventh Day of April 1978

[SEAL]

Attest:

RUTH C. MASON
Attesting Officer

LUTRELLE F. PARKER
Acting Commissioner of Patents and Trademarks